United States Patent
Tuttobene, Jr.

(10) Patent No.: US 6,502,762 B2
(45) Date of Patent: Jan. 7, 2003

(54) PROGRAMMABLE SCENT EMITTER

(76) Inventor: Paul L. Tuttobene, Jr., 84 Benedict Rd., Pittsford, NY (US) 14534

( * ) Notice: Subject to any disclaimer, the term of this patent is extended or adjusted under 35 U.S.C. 154(b) by 29 days.

(21) Appl. No.: 09/871,303

(22) Filed: May 31, 2001

(65) Prior Publication Data

US 2002/0179727 A1 Dec. 5, 2002

(51) Int. Cl.$^7$ .................................................. A61L 9/04
(52) U.S. Cl. ........................... 239/59; 239/55; 239/58; 239/69; 239/70; 43/1; 222/644
(58) Field of Search ................... 239/6, 53, 55, 239/56, 57, 70, 34, 58, 59, 60, 67, 69, 548, 562, 274; 43/1; 222/167, 168, 169, 160, 560, 639, 644, 645, 648

(56) References Cited

U.S. PATENT DOCUMENTS

| | | | | |
|---|---|---|---|---|
| 3,993,444 A | * | 11/1976 | Brown | 239/57 |
| 4,268,285 A | * | 5/1981 | Mason | 239/70 |
| 4,549,693 A | * | 10/1985 | Barlics | 206/5 |
| 4,759,501 A | * | 7/1988 | Silvenis et al. | 239/289 |
| 4,937,431 A | * | 6/1990 | Jameson et al. | 239/59 |
| 4,953,763 A | * | 9/1990 | Kierum et al. | 119/72.5 |
| 5,161,646 A | | 11/1992 | Aurich et al. | |
| 5,299,376 A | | 4/1994 | Roberts | |
| 5,746,019 A | | 5/1998 | Fisher | |
| 5,970,643 A | | 10/1999 | Gawel, Jr. | |
| 6,050,551 A | * | 4/2000 | Anderson | 239/56 |
| 6,085,989 A | | 7/2000 | Cox | |
| 6,102,301 A | | 8/2000 | Tiedemann | |
| 6,241,161 B1 | * | 6/2001 | Corbett | 222/187 |
| 6,340,120 B1 | * | 1/2002 | Seymour | 239/34 |

* cited by examiner

Primary Examiner—Steven J. Ganey
Assistant Examiner—Darren W Gorman
(74) Attorney, Agent, or Firm—Joseph P. Gastel

(57) ABSTRACT

A deer scent emitter including a housing, a scent container in the housing, at least one first opening in the housing, at least one second opening in the scent container, a timer in the housing, and a linkage coupling the timer to the scent container for periodically effecting communication between the first and second openings.

11 Claims, 5 Drawing Sheets

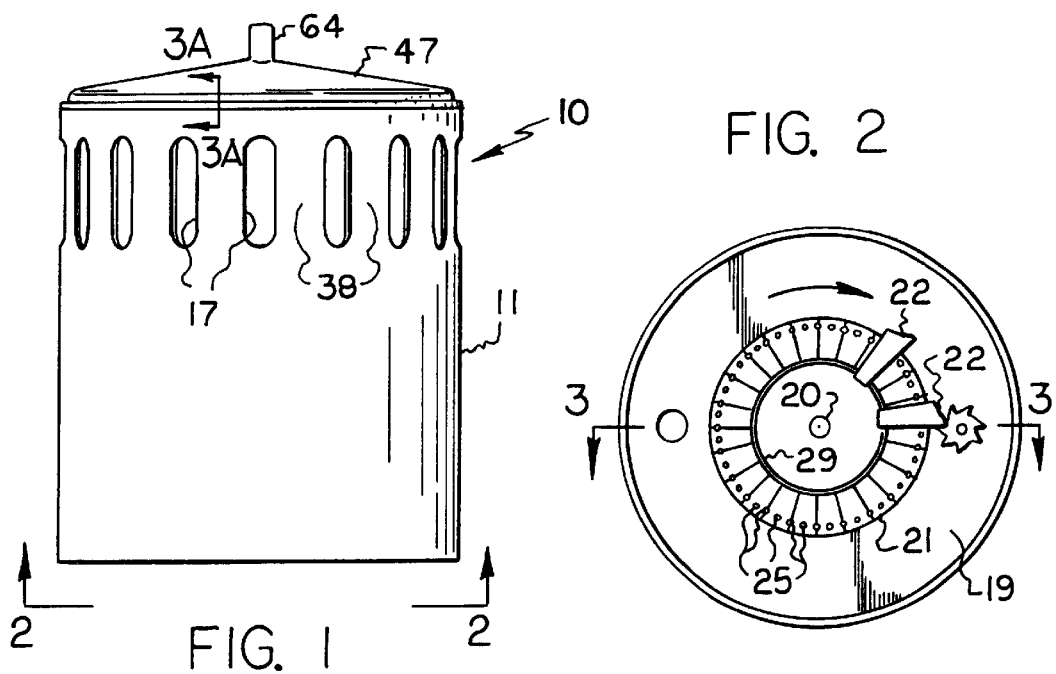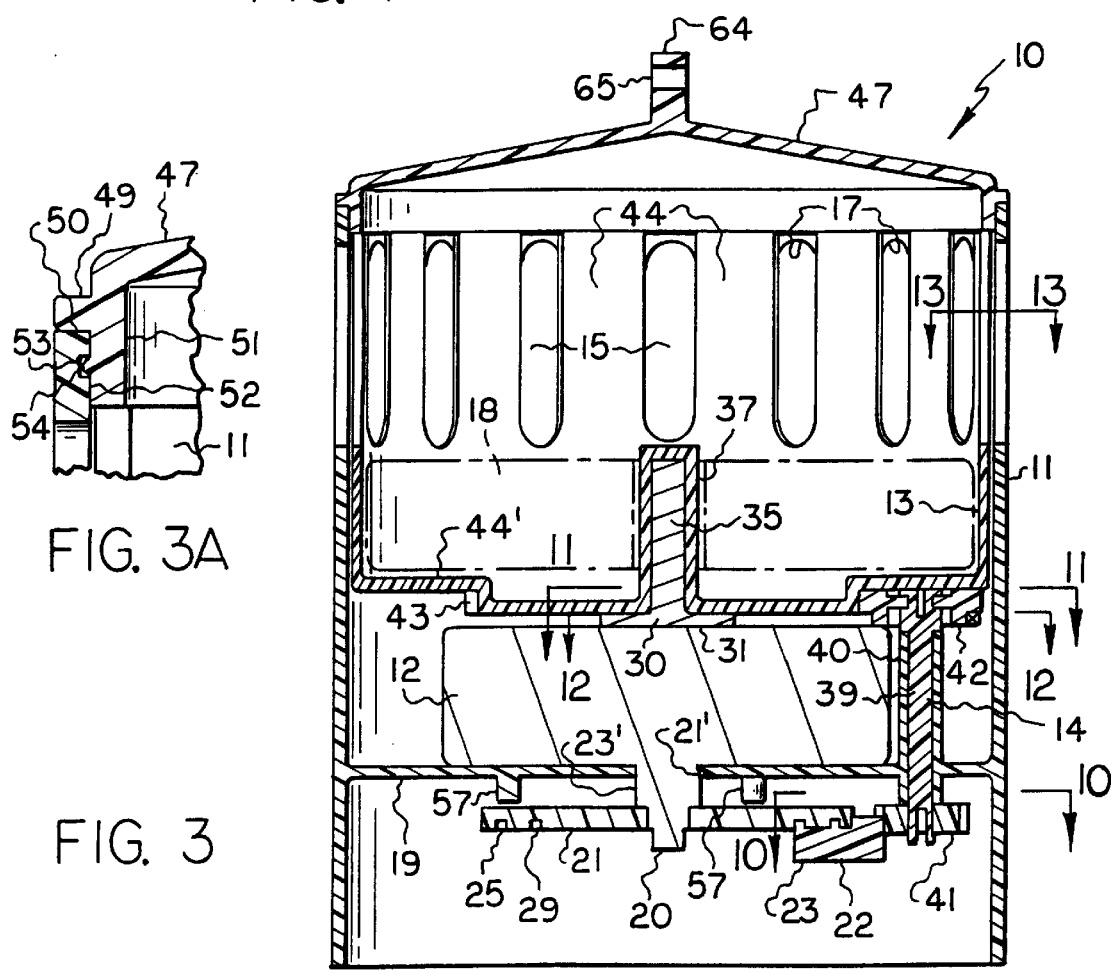

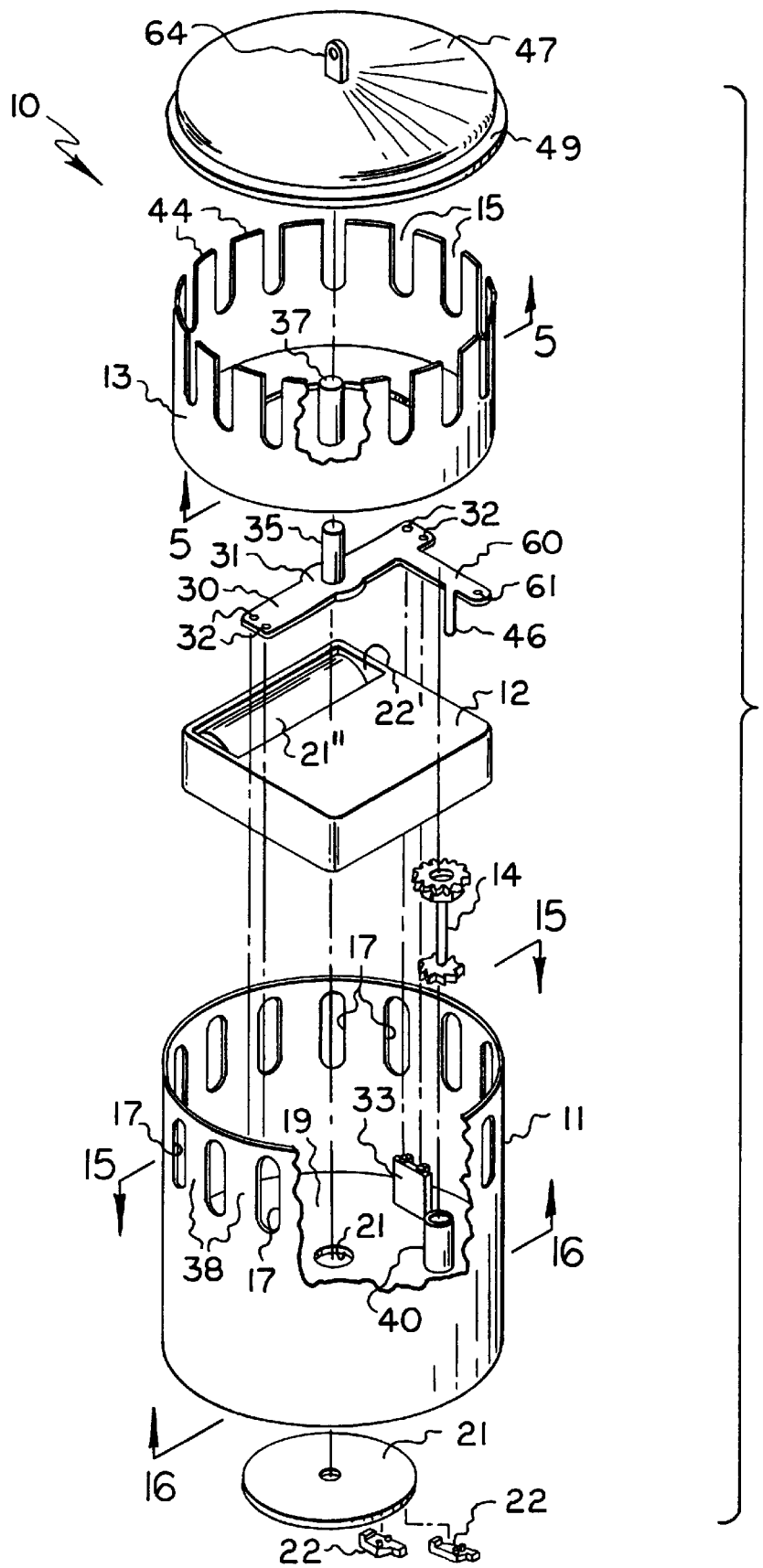

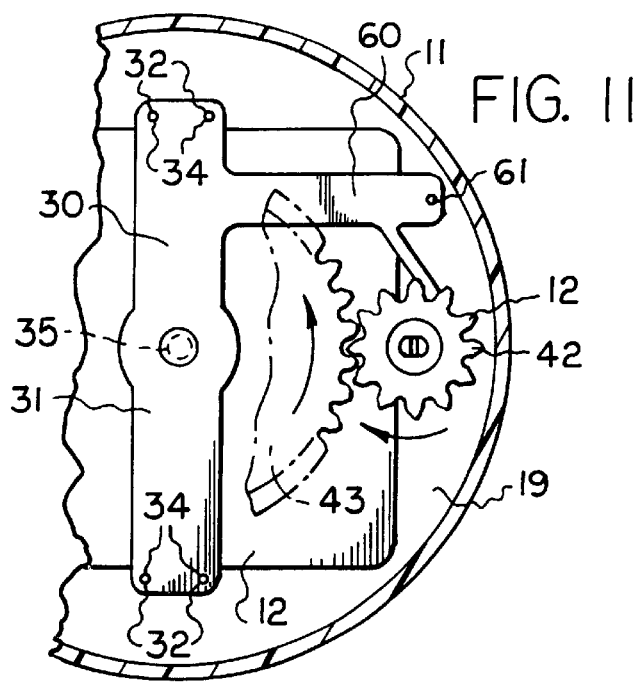
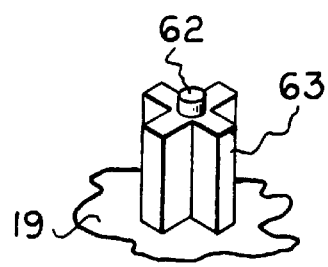
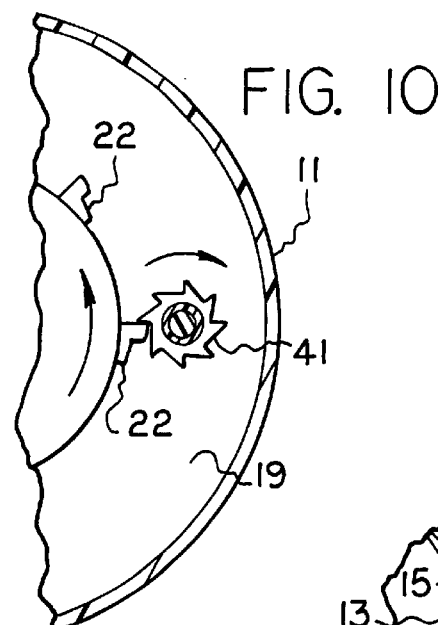
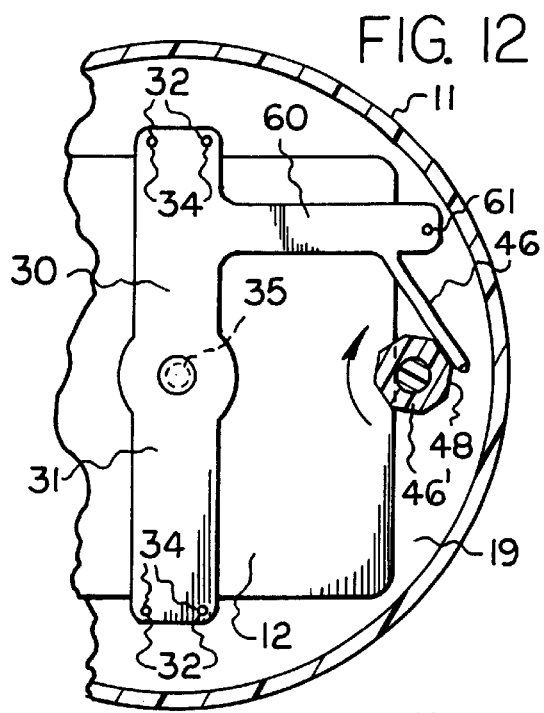
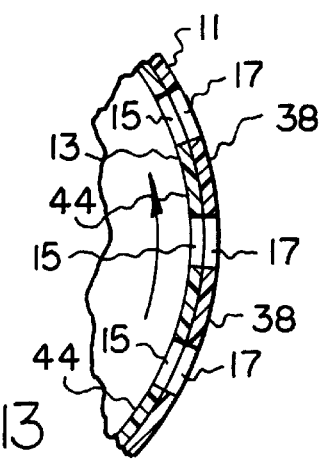
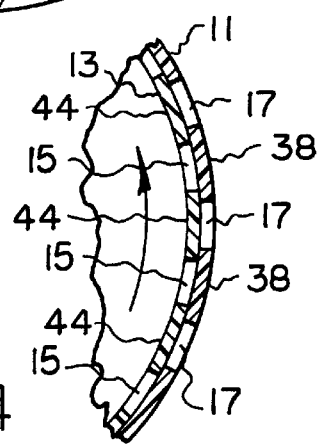

PROGRAMMABLE SCENT EMITTER

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

The present invention relates to a deer scent emitter which can be programmed to emit a deer scent at the same time daily, and when it is not emitting the scent, it will keep the scent confined so that it is not wasted.

By way of background, as is well known, hunters use deer scent to attract deer, and it is desirable to have this scent emitted without the hunter disturbing the scent emitting area. Also, it is desirable to have the scent emitted at regularly spaced time intervals, and when it is not being emitted, it should positively be prevented from being emitted.

BRIEF SUMMARY OF THE INVENTION

It is one object of the present invention to provide a deer scent emitter which can be programmed to expose scent to the atmosphere for the same period of time daily and which will positively prevent the scent from being emitted during other times. Other objects and attendant advantages of the present invention will readily be perceived hereafter.

The present invention relates to a deer scent emitter comprising a housing, a scent container in said housing, at least one first opening in said housing, at least one second opening in said scent container, a timer motor in said housing, and a linkage coupling said timer motor to said scent container for periodically moving said container to effect communication between said first and second openings.

The present invention also relates to a method of producing a deer scent comprising the steps of placing a supply of deer scent at a location to which deer are to be attracted, and alternately periodically exposing the deer scent to the atmosphere and preventing the deer scent from being exposed to the atmosphere.

The various aspects of the present invention will be more fully understood when the following portions of the specification are read in conjunction with the accompanying drawings wherein:

BRIEF DESCRIPTION OF THE SEVERAL VIEWS OF THE DRAWING

FIG. 1 is a side elevational view of the scent emitter of the present invention;

FIG. 2 is a bottom plan view taken substantially in the direction of arrows 2—2 of FIG. 1;

FIG. 3 is an enlarged cross sectional view taken substantially along line 3—3 of FIG. 2;

FIG. 3A is a fragmentary enlarged cross sectional view taken substantially along line 3A—3A of FIG. 1 and showing the joint between the housing and the cap;

FIG. 4 is an exploded view of the scent emitter with certain parts broken away;

FIG. 10 is a fragmentary cross sectional view taken substantially along line 10—10 of FIG. 3;

FIG. 11 is a fragmentary cross sectional view taken substantially along line 11—11 of FIG. 3;

FIG. 12 is a fragmentary cross sectional view taken substantially along line 12—12 of FIG. 3;

FIG. 13 is a fragmentary cross sectional view taken substantially along line 13—13 of FIG. 3 and showing the relative positions of the housing and scent container in a scent emitting position;

FIG. 14 is a fragmentary cross sectional view taken substantially along line 13—13 of FIG. 3 and showing the relative positions of the housing and the scent container in a non-scent emitting position;

FIG. 15B is a fragmentary perspective view of another post to which a portion of the timer securing member is attached;

DETAILED DESCRIPTION OF THE INVENTION

Figure 5:
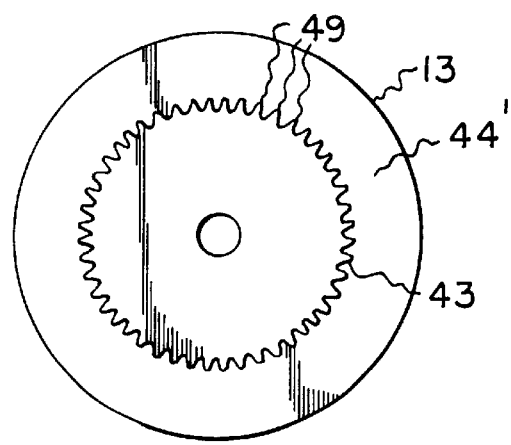
FIG. 5 is a bottom plan view of the scent container.

Summarizing briefly in advance, the deer scent emitter of the present invention automatically emits deer scent at the same time every day without requiring the hunter to be in the area, thereby conditioning a buck to visit this area during this time period. When the deer scent is not being emitted, it is totally confined within the deer scent emitter and therefore is not wasted. In addition, the deer scent emitter is conveniently refillable as required.

Summarizing further in advance, the deer scent emitter 10 includes certain major component parts which achieve the foregoing ends. These major parts are a housing 11 which contains a timer 12 which periodically rotates a scent container in the form of basket 13 through a gear linkage 14 to cause openings 15 of container 13 to align with openings 17 of housing 11 to thereby permit the scent which is contained in porous pad 18 to pass through aligned openings 15 and 17 to thereby emit a scent. After a preset period has elapsed, the timer 12 causes the scent container to move to a position wherein the openings 15 and 17 are no longer aligned and thus the emission of the scent is positively terminated.

In its more specific aspects, the scent emitter 10 includes a cylindrical housing 11 fabricated of molded polypropylene having a circular shelf 19 integrally molded therewith. The timer 12 sits on shelf 19, and its shaft 20 protrudes through aperture 21 in shelf 19. A nut 23' is threaded onto timer shaft 20 to retain it in position on shelf 19. Timer 12 includes a timer motor which is driven by a AA size battery 21'' received in a pocket 22' (FIG. 4) of timer 12. Timer 12 is a commercially obtainable unit which is manufactured by the Young Town Enterprises, Ltd. and is Model No. 12888SH.

Figure 17:
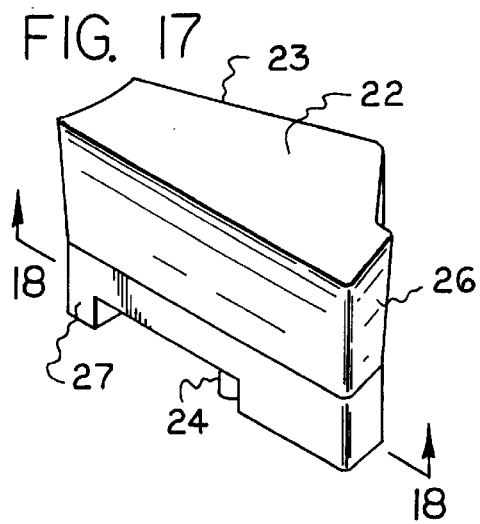
FIG. 17 is a perspective view of the finger which engages the Geneva gear.
Figure 19:
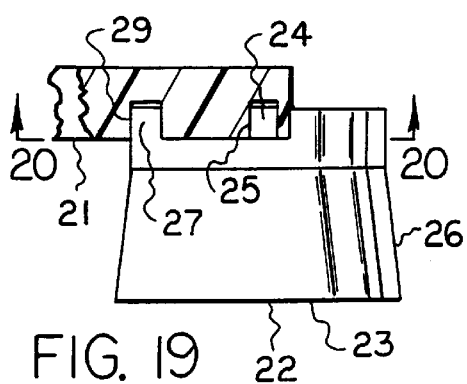
FIG. 19 is a fragmentary enlarged cross sectional view of a portion of FIG. 3 showing the finger mounted on the wheel which is driven by the timer.
Figure 20:
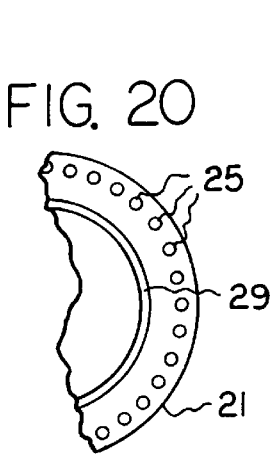
FIG. 20 is a fragmentary view of the finger supporting wheel taken substantially in the direction of arrows 20—20 of FIG. 19.
Figure 18:
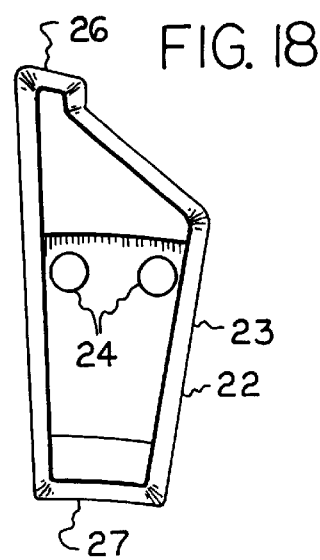
FIG. 18 is a bottom plan view of the finger which engages the Geneva gear taken substantially in the direction of arrows 18—18 off FIG. 17.

A linkage driven by timer 12 periodically moves scent container 13 in increments of a circular motion. A finger-supporting wheel 21 is keyed to timer shaft 20 with a press-fit and fingers 22 can be selectively installed at various positions along its periphery. In this respect, each finger 22 (FIGS. 17–19) includes a body 23 having pins 24 which are received in bores 25 in the underside of wheel 21. Also each finger 22 has a curved rim 27 which is received in groove 29 of wheel 21. The wheel 21 will make a complete rotation every twenty-four hours, and the pins 24 of each finger 22 are inserted in select bores 25 to cause the fingers to perform two functions, namely, to drive the gear linkage (1) to cause the scent container 13 to move to an open position and (2) to cause the scent container 13 to move to a closed position.

The scent container 13 is rotatably mounted within housing 11 in the following manner by member 30 which is a combined timer securing member, scent container post, and gear engaging part (FIGS. 4, 11 and 12). Member 30 includes an elongated section 31 having apertures 32 at its opposite ends. The elongated portion 31 of member 30 bears downwardly on timer 12, and its ends are mounted on the two opposite posts 33 having pins 34 which are received in apertures 32 of member 30. Posts 33 are located adjacent the opposite sides of timer 12. Thus, the portion 31 of member 30 holds timer 12 in position between spaced posts 33. Member 30 includes a post 35 which extends upwardly from elongated portion 31, and post 35 is received in hollow cylindrical central portion 37 of scent container 13 (FIG. 3). Thus post 35 mounts scent container 13 for rotation.

Figure 6:
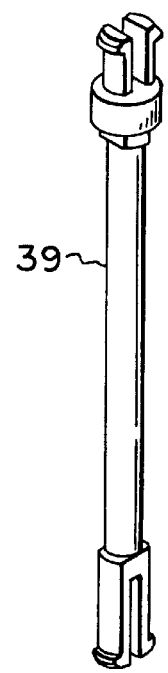
FIG. 6 is a perspective view of the shaft which mounts the various gears.
Figure 7:
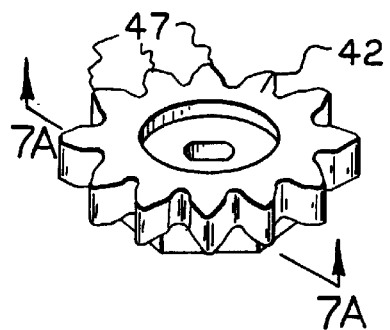
FIG. 7 is a perspective view of the pinion which meshes with the gear on the scent container.
Figure 7A:
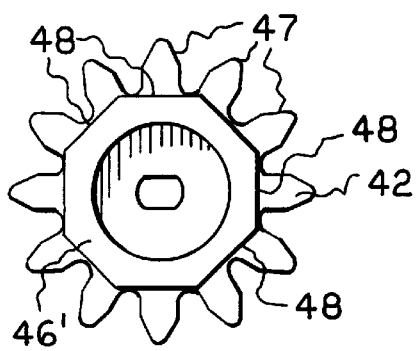
FIG. 7A is a bottom plan view of the pinion of FIG. 6 taken substantially in the direction of arrows 7A—7A of FIG. 7.
Figure 8:
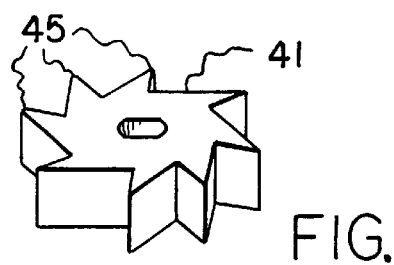
FIG. 8 is a perspective view of the Geneva gear which is driven by the timer motor.
Figure 9:
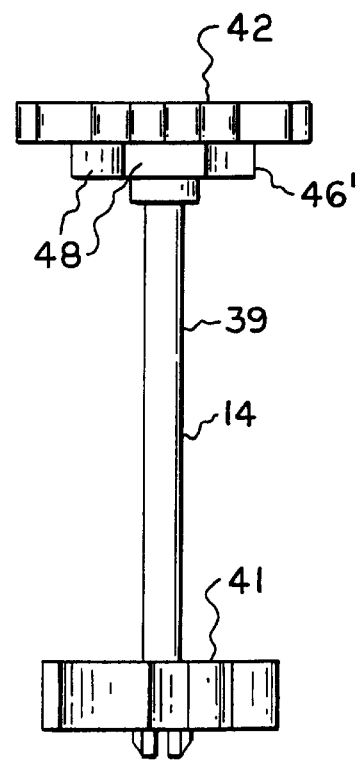
FIG. 9 is a side elevational view of the assembly containing the parts of FIGS. 6–8.

Basket 13 is rotated in increments between its scent emitting position (FIG. 13) and its closed position (FIG. 14) in the following manner. Gear assembly 14 couples timer 12 to scent container 13 through wheel 21 and fingers 22. In this respect, stem 39 (FIGS. 3, 6 and 9) is journaled in tube 40 which is formed integrally with shelf 19. A Geneva gear 41 (FIGS. 3, 8, 9 and 10) is keyed to the bottom of stem 39. A pinion 42 (FIGS. 3, 7, 7A, 9 and 11) is keyed to the top of shaft 39. Pinion 42 is in engagement with gear 43 which is molded integrally with the bottom side 44' of scent container 13 (FIGS. 3 and 5).

The scent container 13 is moved from its closed position of FIG. 14 to its open position 13 in the following manner. In this respect, housing 11 has sixteen openings 17 spaced 22.5° apart, and there are sixteen spaced closed sections 38 between openings 17. There are also sixteen openings 15 in scent container 13 spaced 22.5° apart. There are also sixteen spaced closed sections 44 between openings 15. Geneva gear 41 (FIGS. 3, 8 and 9) has eight teeth 45. Thus, when a finger 22 engages Geneva gear 41, it will rotate it 45° which, in turn, will rotate pinion 42 45°. Pinion 42 has twelve teeth 47 which mesh with gear 43 which has forty-eight teeth 49. Thus, when Geneva gear 41 having eight teeth 45 rotates 45°, gear 42 will also rotate 45° and gear 43 will rotate one-fourth of 45°, namely, 11.25°. Since the openings 15 and 17 of scent container 13 and housing 11 are both 22.50° apart, the rotation of scent container 13 11.25° will cause the openings 15 and 17 of the scent container and housing, respectively, to become aligned. At this time the scent which is contained in porous disc 18 can be in communication with the atmosphere through the overlapping openings 15 and 17 of the scent container 13 and housing 11, respectively.

The openings 15 and 17 will remain in overlapping relationship until the second finger 22 engages Geneva gear 41 and thus moves Geneva gear 41 through 45° whereupon the pinion 42 will move gear 43 through 11.25° to thereby cause the portions 38 of housing 11 to overlie the openings 15 of scent container 13, thereby closing off the scent containing pad 18 from the atmosphere. The scent containing pad 18 will remain closed off from the atmosphere until the Geneva gear 41 is again engaged by finger 22, as described above to thereby repeat the opening and closing cycles between scent container 13 and housing 11.

The scent emitter 10 includes a cap 47 which is mounted on housing 11 as depicted in FIG. 3A. In this respect, cap 47 has an annular rim 49 which overlies the annular edge 50 of housing 11. Additionally, cap 47 has an annular portion 51 which fits closely with the annular rim 52 of housing 11. An annular bead 53 of rim 51 is received in an annular groove 54 of rim 52. The bead-groove structure 53–54 is sufficient to hold cap 47 assembled on housing 11 but cap 47 can be removed by applying sufficient force thereto in the event it is necessary to replace scent holding pad 18. However, normally scent can be replaced to porous pad 18 by injecting it through aligned openings 15, 17. A loop portion 64 is formed integrally with cap 47, and it has an opening 65 for receiving a string used to suspend the cap from an external member, such as a tree branch.

Figure 15:
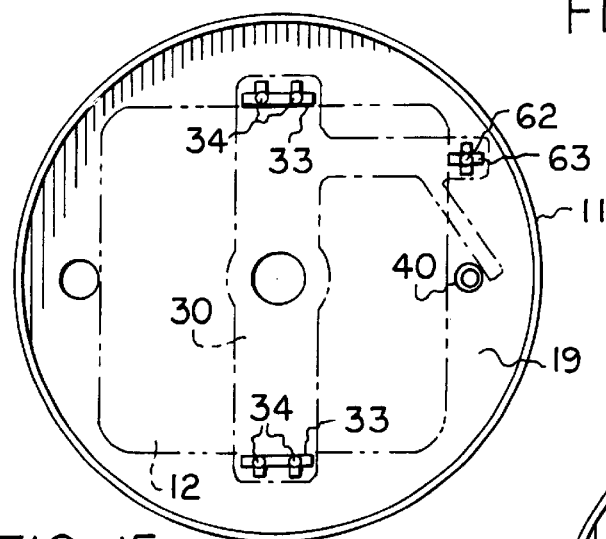
FIG. 15 is a plan view of the housing taken substantially in the direction of arrows 15—15 of FIG. 4 and showing the housing shelf with the timer and the timer securing member in phantom thereon.
Figure 15A:
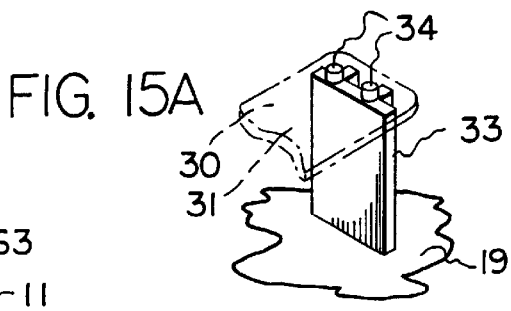
FIG. 15A is a fragmentary perspective view of a post to which the timer-securing member is attached to lock the timer in position.

Structure is provided for maintaining the scent container 13 in the position to which it was last placed. In this respect, member 30 (FIG. 12) includes an arm 60 which extends outwardly from portion 31 thereof. The outer end of arm 60 includes an aperture 61 (FIG. 11) which receives pin 62 (FIGS. 15 and 15B) at the outer end of post 63 extending upwardly from shelf 19. A flexible finger 46 (FIG. 12) extends outwardly from arm 60, and it sequentially engages each straight side 48 (FIG. 7A) of the octagonal part 46' which is formed integrally with pinion 42. Thus, flexible finger 46 will retain the gear assembly 14 in the position to which it was last moved but it will deflect to permit it to move 45° as required when the Geneva gear is moved 45° by a finger 22.

Figure 16:
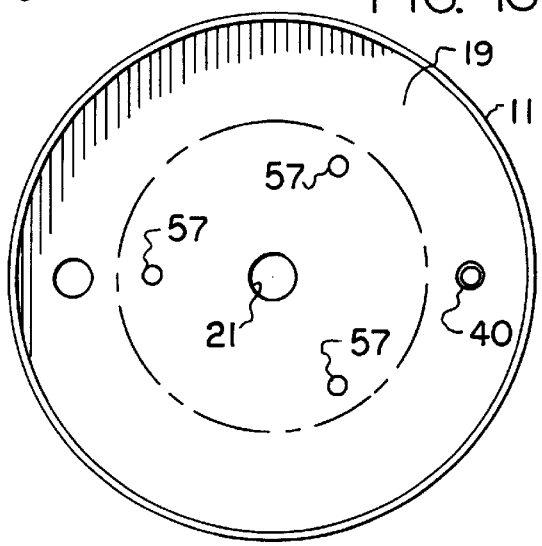
FIG. 16 is a bottom plan view of the housing taken in the direction of arrows 16—16 of FIG. 4 and showing the structure on the underside of the shelf.

Structure is provided for preventing wheel 21 from cocking excessively when the fingers 22 are inserted into it. In this respect, three small posts 57 (FIGS. 3 and 16) are molded integrally with the underside of shelf 19 and they are spaced 120° apart. Thus, when pressure is applied to the underside of wheel 21, posts 57 will tend to prevent it from deflecting excessively.

The body 11 and the scent container 13 and cap 47 are fabricated of polypropylene. The remainder of the parts exclusive of the timer 12 are fabricated of the plastic known under the trademark DELRIN.

While preferred embodiments of the present invention have been disclosed, it will be appreciated that it is not limited thereto but may be otherwise embodied within the scope of the following claims.

What is claimed is:

1. A deer scent emitter comprising a housing, a scent container in said housing, at least one first opening in said housing, at least one second opening in said scent container, a timer in said housing, and a linkage coupling said timer to said scent container for periodically moving said scent container to effect communication between said first and second openings.

2. A deer scent emitter as set forth in claim 1 including a plurality of first openings in said housing, and a plurality of second openings in said scent container.

3. A deer scent emitter as set forth in claim 2 wherein said housing includes a cylindrical portion, and wherein said first openings are located in said cylindrical portion of said housing, and wherein said scent container includes a cylindrical portion, and wherein said second openings are located in said cylindrical portion of said scent container, and wherein said cylindrical portion of said scent container is in complementary mating relationship with said cylindrical portion of said housing.

4. A deer scent emitter as set forth in claim 3 wherein said timer rotates said scent container relative to said housing through said linkage.

5. A deer scent emitter as set forth in claim 4 wherein said first openings are spaced on said cylindrical portion of said housing with housing portions therebetween, and wherein said second openings are spaced on said cylindrical portion of said scent container with scent container portions therebetween, and wherein said scent container portions and said housing portions are periodically in overlapping relationship with said first and second openings, respectively, to effect lack of communication between said first and second openings.

6. A deer scent emitter as set forth in claim 5 wherein said scent container includes a gear affixed thereto, and wherein said linkage comprises a gear assembly coupled to said gear.

7. A deer scent emitter as set forth in claim 5 including a first member coupled to said timer for actuating said linkage to move said scent container to a position wherein said first and second openings are in communication, and a second member coupled to said timer motor for actuating said linkage to move said scent container to a position wherein said first and second openings are not in communication.

8. A deer scent emitter as set forth in claim 7 including a shelf in said housing, and wherein said timer is mounted on said shelf.

9. A deer scent emitter as set forth in claim 8 wherein said scent container includes a bottom and is located above said timer, and a timer shaft coupled to said bottom.

10. A deer scent emitter as set forth in claim 9 wherein said gear is affixed to said bottom.

11. A deer scent emitter as set forth in claim 10 wherein said gear assembly comprises a shaft journaled in said shelf, a Geneva type gear mounted on said shaft in operative relationship to said first and second members, and a pinion mounted on said shaft in engagement with said gear.

* * * * *